(12) United States Patent
Ziran

(10) Patent No.: US 9,381,052 B2
(45) Date of Patent: Jul. 5, 2016

(54) DYNAMIC AXIAL NAIL FOR INTRAMEDULLARY TREATMENT OF LONG BONE FRACTURES

(71) Applicant: Navid Ziran, Santa Monica, CA (US)

(72) Inventor: Navid Ziran, Santa Monica, CA (US)

( * ) Notice: Subject to any disclaimer, the term of this patent is extended or adjusted under 35 U.S.C. 154(b) by 0 days.

(21) Appl. No.: 14/077,055

(22) Filed: Nov. 11, 2013

(65) Prior Publication Data

US 2014/0135769 A1    May 15, 2014

Related U.S. Application Data

(60) Provisional application No. 61/725,429, filed on Nov. 12, 2012.

(51) Int. Cl.
*A61B 17/56* (2006.01)
*A61B 17/72* (2006.01)

(52) U.S. Cl.
CPC .................................. *A61B 17/72* (2013.01)

(58) Field of Classification Search
CPC ............... A61B 17/72; A61B 17/7216; A61B 17/7225; A61B 17/7233; A61B 17/74; A61B 17/744; A61B 17/68; A61B 17/7208–17/7241
USPC ............................... 606/60, 62, 63, 64, 68, 99
See application file for complete search history.

(56) References Cited

U.S. PATENT DOCUMENTS

| 2,397,545 A | 2/1945 | Hardinge |
| 2,672,861 A | 12/1952 | Jonas et al. |
| 3,441,017 A | 4/1969 | Kaessmann |
| 3,807,394 A | 4/1974 | Attenborough |
| 3,986,504 A | 10/1976 | Avila |
| 4,237,875 A | 12/1980 | Termanini |
| 5,415,660 A * | 5/1995 | Campbell et al. ............... 606/62 |
| 5,505,734 A * | 4/1996 | Caniggia et al. ............... 606/63 |
| 5,516,335 A | 5/1996 | Kummer et al. |
| 5,871,484 A | 2/1999 | Spievack et al. |
| 6,197,065 B1 | 3/2001 | Martin et al. |
| 6,508,841 B2 | 1/2003 | Martin et al. |

(Continued)

FOREIGN PATENT DOCUMENTS

| CN | 1813639 | 8/2006 |
| CN | 101224133 | 7/2008 |

(Continued)

OTHER PUBLICATIONS

International Search Report dated Jan. 30, 2014.

(Continued)

*Primary Examiner* — Jacqueline Johanas
*Assistant Examiner* — Tessa Matthews
(74) *Attorney, Agent, or Firm* — Rutan & Tucker LLP; John K. Fitzgerald

(57) ABSTRACT

An intramedullary nail for fixation and stabilization of a fractured bone that also allows for a controlled amount of longitudinal motion at the fracture site to encourage bone remodeling and healing is described. The intramedullary nail has a proximal portion and a distal portion that are coupled together in a manner by a biasing assembly that provides for a controlled movement of the proximal and distal portions relative to each other so that when a patient puts pressure on the bone, such as when walking, the fracture site compresses and the bone ends move together, and when the pressure is released from the bone, the bone ends are biased apart by a controlled amount.

14 Claims, 8 Drawing Sheets

(56) References Cited

U.S. PATENT DOCUMENTS

| | | | |
|---|---|---|---|
| 6,706,053 B1* | 3/2004 | Boylan et al. | 606/200 |
| 6,712,855 B2 | 3/2004 | Martin et al. | |
| 6,808,527 B2 | 10/2004 | Lower et al. | |
| 7,141,073 B2 | 11/2006 | May et al. | |
| 7,476,254 B2 | 1/2009 | White et al. | |
| 7,722,678 B2 | 5/2010 | Brown et al. | |
| 2003/0032958 A1* | 2/2003 | Soubeiran | 606/61 |
| 2005/0159749 A1* | 7/2005 | Levy | A61B 17/68 606/62 |
| 2006/0129247 A1 | 6/2006 | Brown et al. | |
| 2006/0173457 A1 | 8/2006 | Tornier | |
| 2008/0183171 A1 | 7/2008 | Elghazaly et al. | |
| 2008/0269808 A1* | 10/2008 | Gall et al. | 606/299 |
| 2009/0182336 A1* | 7/2009 | Brenzel et al. | 606/62 |
| 2009/0228007 A1* | 9/2009 | Justin et al. | 606/62 |
| 2009/0270874 A1* | 10/2009 | Santarella | A61F 2/3609 606/99 |
| 2011/0000344 A1* | 1/2011 | Summers | G01B 3/28 81/429 |
| 2011/0004246 A1* | 1/2011 | Haaja et al. | 606/246 |
| 2011/0230883 A1* | 9/2011 | Zahrly | A61B 17/7216 606/63 |
| 2012/0130370 A1* | 5/2012 | Kinmon | 606/62 |
| 2012/0136356 A1 | 5/2012 | Doherty et al. | |
| 2012/0179215 A1* | 7/2012 | Soubeiran | 606/86 R |
| 2013/0136356 A1* | 5/2013 | Hughes | 382/167 |
| 2013/0296859 A1* | 11/2013 | Walker et al. | 606/60 |
| 2013/0325008 A1* | 12/2013 | Kuxhaus | A61B 17/7233 606/63 |
| 2014/0128868 A1* | 5/2014 | Harrison et al. | 606/60 |

FOREIGN PATENT DOCUMENTS

| | | |
|---|---|---|
| EP | 1685803 | 8/2006 |
| WO | 2006116164 A1 | 11/2006 |
| WO | WO 2009/002890 | 12/2008 |

OTHER PUBLICATIONS

Trafton, Peter G., M.D., Tibial Shaft Fractures, Elsevier Science (USA), 2003; Chapter 57, pp. 2131-2255.

Ozcivici, Engin, Mechanical Signals as Anabolic Agents in Bone, www.nature.com/nrrheum, Jan. 2010, vol. 6, pp. 50-59.

Leucht, Philipp, Effect of Mechanical Stimuli on Skeletal Regeneration Around Implants, National Institutes of Health, Apr. 2007, vol. 40(4); pp. 919-930, NIH Public Access.

Goodship, Allen E., BVSc, PhD, MRCVS, Strain Rate and Timing of Stimulation in Mechanical Modulation of Fracture Healing, Clinical Orthopedics and Related Research, 1998, No. 355S, pp. S106-S115.

Spadaro, Joseph A., Review Mechanical and Electrical Interactions in Bone Remodeling, Bioelectromagnetics, 1997, vol. 18, pp. 193-202.

Buhren, Volker, T2 TM Tibial Nailing System, Stryker, 2004, pp. 1-32.

Anderson, J.C., Electrical Properties of Wet Collagen, National Publishing Group, Apr. 1968, vol. 281, pp. 166-168.

Kenwright, J., Axial Movement and Tibial fractures, The Journal of Bone and Joint Surgery, Jul. 1991, vol. 73-B, , No. 4, pp. 654-659.

Ehrlich, Mes Strain and Bone Cell function: A Review, Osteoporosis International, 2002, vol. 13, pp. 688-700.

Peltier, A brief historical note on the use of electricdial in the treatment of fractures, Clinical Orthopedics and related Research, 1981, vol. 161, pp. 4-7.

ASTM International, Standard Specification and Test Methods for Intermedullary Fixation Devices, 2007, pp. 1-18.

Weis, Comparison of microCT and an inverse finite element approach for biochemical analysis: Results in mesenchymal stem cell therapeutic system for fracture healing, Journal of Biomechanics, 2012, vol. 45, pp. 2164-2170.

Friendbrerg, Bioelectric Potentials in Bone, Jul. 1966, vol. 48-A, , No. 5, pp. 915-923.

Fukada, Electrical Phenommenta, in Biorheology, 1982, vol. 19, pp. 15-27.

Fukada, One the Piezoelectric Effect on Bone. Journal of Physical Society of Japan, Oct. 1957, vol. 12, No. 10, pp. 1158-1162.

Hastings, Electrical Effects in the Bone, Journal of Biomechanics, Nov. 1987, vol. 10, pp. 515-521.

Bong, The History of Intramulledullary Nailing, Bulletin of BYU Hospital for Joint Diseases, 2006, vol. 64, Nos. 3 and 4, pp. 94-97.

Walsh, Ion concentration effects on the bone streaming potentionals and seta potentials, Biomaterials, May 1992, vol. 14, pp. 331-336.

Schenider, Loads Acting in an Intramedullar Nail During Fracture Healing in the Human Femur, Journal of Biomechanics 2001, vol. 34, pp. 849-857.

McDonald, F., An in vivo assessment of muscular activity and the importance of electrical phenomena in bone remodeling, Journal Anat. 1990, vol. 172, pp. 165-175.

Piekarski, K., Osteogenetic Stimulation by Externally Applied DC Current, Acta Ortho., 1978, vol. 49, pp. 113-120.

Spadora, Joseph, Mechanical and Electrical Interactions in Bone Remolding, Bioelectronicmagnetics, 1997, vol. 18, pp. 193-202.

Goodship, A., The Influence of Induced Micromovement Upon the Healing of Experimental Tibial Fractures, The Journal of Bone and Joint Surgery, Aug. 1985, vol. 67-B, pp. 650-655.

Spadora, Joseph, Mechanicals Factors in Electrode-Induced Osteogenesis, Journal of Orthopedic Research, 1986, vol. 4, pp. 37-44.

Preininger, Bernd, Spatial-Temporal Mapping of Bone Structural and Elastic Properties in a Sheep Model Following Osteotomy, Ultrasound in Med. & Biol., 2011, vol. 37, No. 3, pp. 473-484.

Ahn, Andrew, Relevance of Collagen Piezoelectricity to "Wolff s Law": A Critical Review, NIH Public Access, Sep. 2009, vol. 7, No. 3, pp. 733-741.

Kawamura, Haruo, Stimulatory effect on zinc-releasing calcium phosphate implant on bone formation in rabbit femora, Jun. 1999, pp. 184-190.

Yu, Jiangming, In Vitro and In Vivo Evaluation of Zinc-Modified Ca—Si-Based Ceramic Coating for Bone Implants, PLOS One, Mar. 2013, vol. 8, No. 3, pp. 1-10.

Tanaka, Shiego, Bone Formation Induced by a Novel Form of Mechanical Loading on Joint Tissue, Biological Sciences in Space, 2004, vol. 18, No. 2, pp. 41-44.

Hastings, GW, Electrical Effects in Bone, Journal of Biomedical Engineering, 1988vol. 10, Issue 6, pp. 515-521.

Habibovic, P., Bioinorganic and biomaterials: bone repair, Acta Biomaterial, 2011, vol. 7, pp. 3013-3026.

Hu, H., Antibacterial activity and increased bone marrow stem cell functions of Zn-incorporated TiO2 coatings on titanium, Acta Biomaterialia, 2012, vol. 8, pp. 904-915.

Kwun, In-Sook, Zinc deficiency suppresses matrix mineralization and retards osteogensis transiently with catch-up possibly through Runx 2 modulation, Bone, 2010, vol. 46, pp. 732-741.

Matsui, T., Peptides, Elsevier Science Inc., 1995, vol. 16, No. 6, pp. 1063-1068.

Pollack, Sr., Calcified Tissue International, Springer Verlag, 1984, vol. 36, pp. 77-81.

Fukada, E., Biorheology, IOS Press 1982, vol. 19, pp. 15-27.

Yamaguchi, M., Effect of zinc on gene expression in osteoblastic MC3T3-E1, Molecular and Cellular Biochemistry, 2008, vol. 312, pp. 157-166.

Pienkowski, D., The Origin of Stress-Generated Potentials in Fluid-Saturated Bone, Journal of Orthopedic Research, 1983, vol. 1, pp. 30-41.

Yamaguchi, M., Biochemical Pharmacology, Elsevier Science, Nov. 1987, vol. 36, No. 22, pp. 4007-4012.

Wang, H., In vivo degradation behavior of Ca-deficient hyroxyapatite, Elsevier, Nov. 2011, vol. 88, pp. 254-259.

Brighton, CT, Electrically induced ontogenesis: relationship between char, Clinical Orthopaedics and Related Research, 1981, Issue 161, pp. 122-132.

* cited by examiner

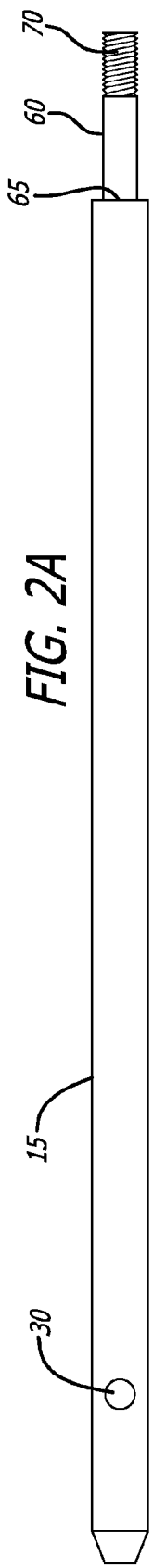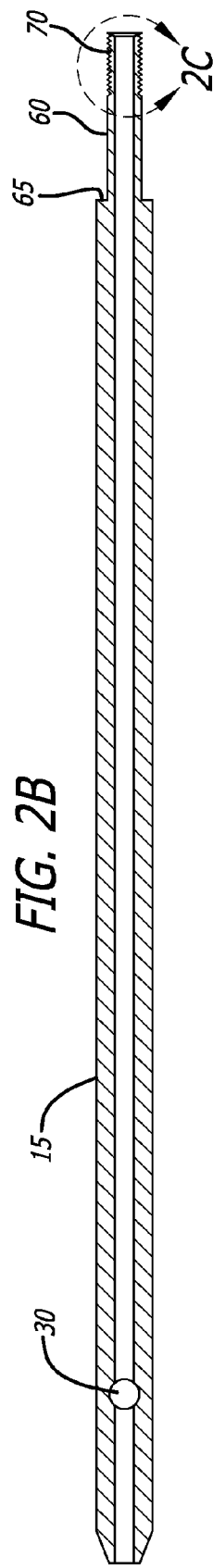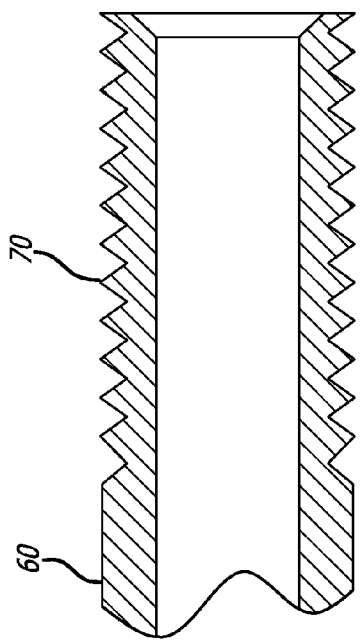

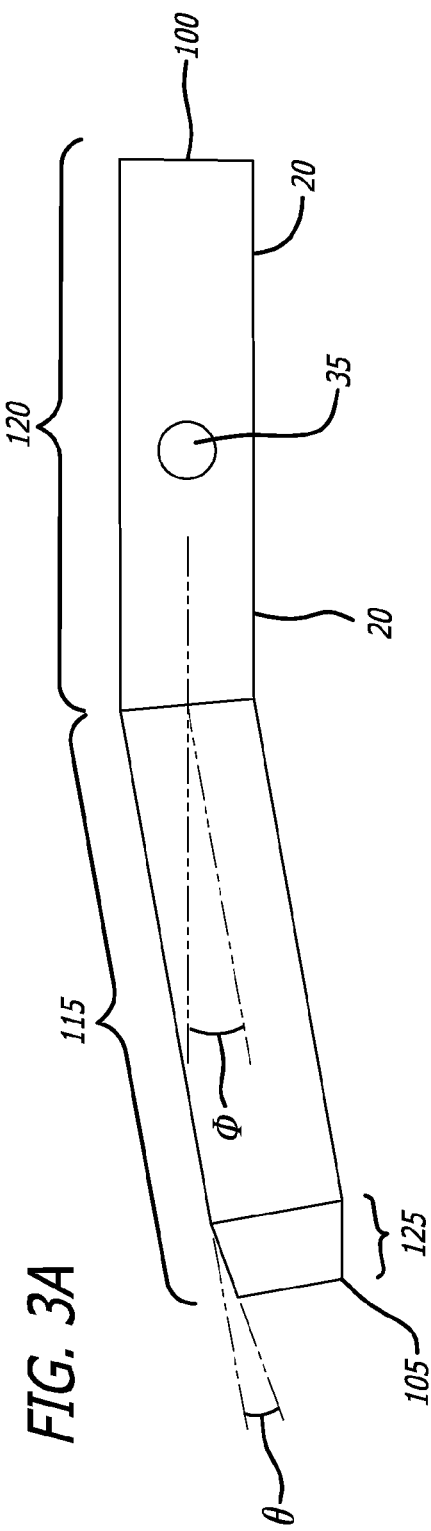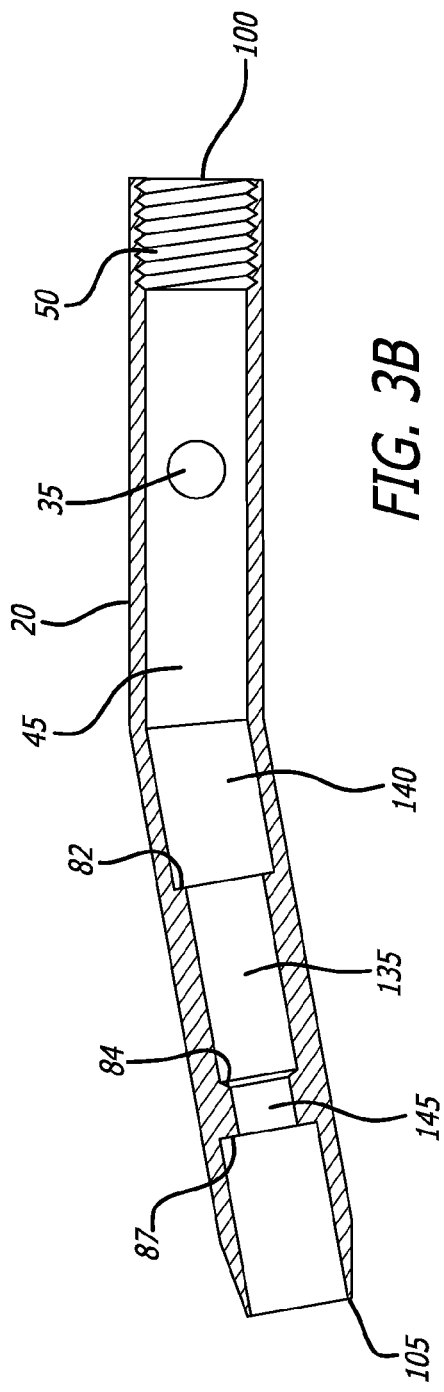
FIG. 3A
FIG. 3B

DYNAMIC AXIAL NAIL FOR INTRAMEDULLARY TREATMENT OF LONG BONE FRACTURES

CROSS-REFERENCES TO RELATED APPLICATIONS

This application claims priority from U.S. Application No. 61/725,429, filed Nov. 12, 2012 incorporated by reference in its entirety.

BACKGROUND

This invention relates to an intramedullary nail for use in stabilizing and enhancing the healing of broken bones, and more particularly to an intramedullary nail that includes motion along its longitudinal axis so as to elicit an improved healing response in the bone in which the nail is placed.

It is well known in the art that functional loading of skeletal bone results in changes to bone quality and quantity. Conversely, lack of mechanical loading has been found to lead to a loss of bone quality and quantity.

When a bone fractures, one of two physiological processes are stimulated that provide for healing of the fracture. The first process is denoted enchondral ossification and occurs when there is strain at the fracture site. This process forms bone through a cartilage intermediate and is similar to the mineralization that occurs at the human growth plate. The second process is denoted intramembranous ossification and occurs when the fracture edges are not only in contact and opposed but also have minimal to no strain, that is, rigid fixation. In this process, little bone callus is seen as the fracture gap is consolidated by cutting "cones" that cross the fracture. Both processes essentially bridge the gap between the fracture elements. The bony healing process in humans takes approximately 6-8 weeks except bones with potentially compromised vascular supply or vascular watershed areas (such as, for example, the tibia, scaphoid, talus, and the like). After the initial healing process, the bone is comprised of woven bone and later remodels to lamellar bone.

Typically, fractured bones are stabilized using various mechanical or surgical means to hold the fractured portions of the bone in alignment. Depending on the gap between the fracture ends, the body forms either granulation tissue (scar tissue), cartilage (enchondral ossification), or bone (intramembranous ossification). If the fracture gap is too large, the body heals via scar tissue—tough connective tissue that resists strain, and while not rigid, this tissue maintains the fragments in proximity to each other. Non-healed fractures, such as those with interposed scar tissue, can cause significant pain for the patient as there is still motion occurring between the previously fractured elements. Surgical intervention with opposition of the bones, possible use of a bone graft, and mechanical stabilization is usually necessary to help the fracture heal.

One means of stabilizing a fractured bone is through the use of an intramedullary nail. For example, where the fracture is located in the tibia bone of the lower leg, the central portion of the bone, known as the medullary canal or space, is accessed. The current convention is to ream the medullary canal prior to insertion of an intramedullary nail. In other cases, the medullary canal may not be reamed.

The intramedullary nail is inserted into the medullary canal and positioned as desired to align the fractured ends or edges of the bone and restore length, alignment, and rotation. Fixation screws, or locking screws, are usually used at both the proximal and distal ends of the nail to ensure that the intramedullary nail is a static construct with rotational stability.

Various authors have posited whether allowing some motion at the fracture site would enhance the healing process by providing mechanical signals that would initiate an anabolic response to spur bone remodeling. The problem, however, is how to allow enough motion at the fracture site to enhance the healing process while still maintaining adequate stabilization of length, alignment, and rotation of the fractured bone ends. If too much motion occurs, the bone may not completely heal.

What has been needed, and heretofore unavailable, is an intramedullary device that provides for adequate positioning and stabilization of the fractured ends or edges of a bone, while still allowing a measure of motion to occur at the fracture site to provide for enhanced healing of the fracture. The present invention satisfies these, and other needs.

SUMMARY OF THE INVENTION

In a most general aspect, the invention provides an intramedullary nail that provides for fixation and stabilization of a fractured bone while still providing a controlled amount of motion in the longitudinal axis at the fracture site to encourage and hasten bone healing.

In another aspect, the present invention includes an intramedullary nail, comprising: a distal portion and a proximal portion; a bias member or device disposed between the distal and proximal portions for biasing the distal and proximal portions apart along a longitudinal axis; and an adjusting assembly configured to engage the distal and proximal portions such that actuation of the adjusting assembly results in providing for a selected amount of motion along the longitudinal axis between the proximal and distal portions. In one alternative aspect, the distal and proximal portions are in a telescoping arrangement relative to each other.

In still another aspect, the adjusting assembly is adjustable to allow a selected amount of motion along the longitudinal axis between the proximal and distal portions of the intramedullary nail, applying a compressive force along the longitudinal axis causes a combined length of the distal and proximal portions to be reduced, and reducing the compressive force allows the combined length of the distal and proximal portions of the intramedullary nail to increase.

In yet another aspect, the invention further includes an alignment assembly that engages the proximal and distal portions of the intramedullary nail in a manner to maintain an alignment between the proximal and distal portions of the intramedullary nail.

In still another aspect, the invention also includes an outer surface of the distal and proximal portions that is covered with a material that enhances healing of a fracture. In one alternative aspect, the material is zinc.

In yet another aspect, the bias member is a spring. In an alternative aspect, the bias member is a compliant membrane.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 2A is a side view of a distal portion of the intramedullary nail of FIG. 1A.

FIG. 2B is a cross-sectional side view of the distal portion of the intramedullary nail of FIG. 2A.

FIG. 2C is a magnified cross-sectional side view of a threaded proximal end of the distal portion of the intramedullary nail shown in of FIG. 2B.

FIG. 3A is a side view of the proximal portion of the intramedullary nail of FIG. 1A.

FIG. 3B is a cross-section of the proximal portion of the intramedullary nail of FIG. 3A showing internal details of the embodiment.

DETAILED DESCRIPTION OF THE PREFERRED EMBODIMENTS

Figure 1A:
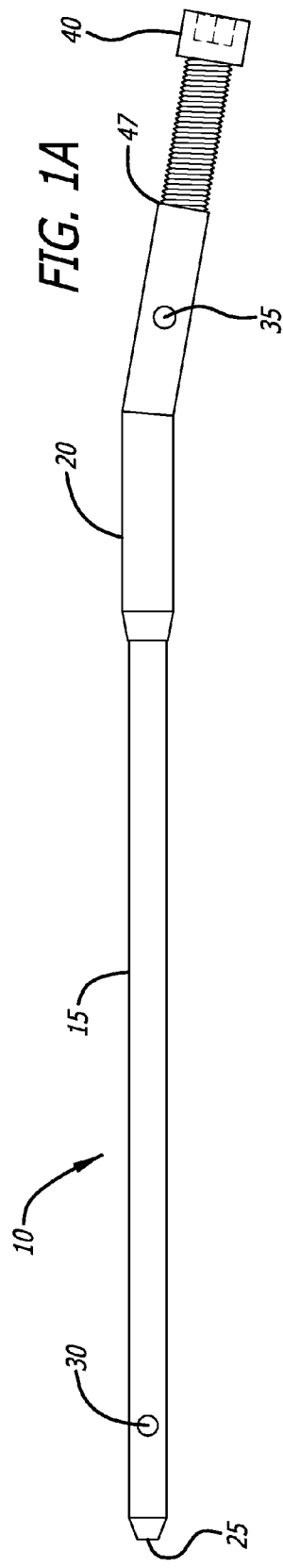
FIG. 1A is a side view of an embodiment of an intramedullary nail in accordance the present invention.

Referring now to the drawings in detail, in which like reference numerals indicate like or corresponding elements among the several figures, there is shown in FIG. 1A an exemplary embodiment of an intramedullary nail 10 in accordance with the present invention. Nail 10 includes a distal portion 15 and a proximal portion 20. As will be discussed in more detail below, the distal and proximal portions are engaged in a manner that allows each portion to move a limited amount independently of the other portion.

Distal portion 15 includes an end port 25 disposed at a distal end of the distal portion 15. A fixation hole 30 is also disposed near the distal end of distal portion 15. Fixation hole 30 is sized to receive a screw or other fastener that may be used to attached distal portion 15 to bone surrounding distal portion 15 when the nail 10 is positioned within the medullary space of a bone so as to fixate and stabilize a fracture in the bone.

Figure 1B:
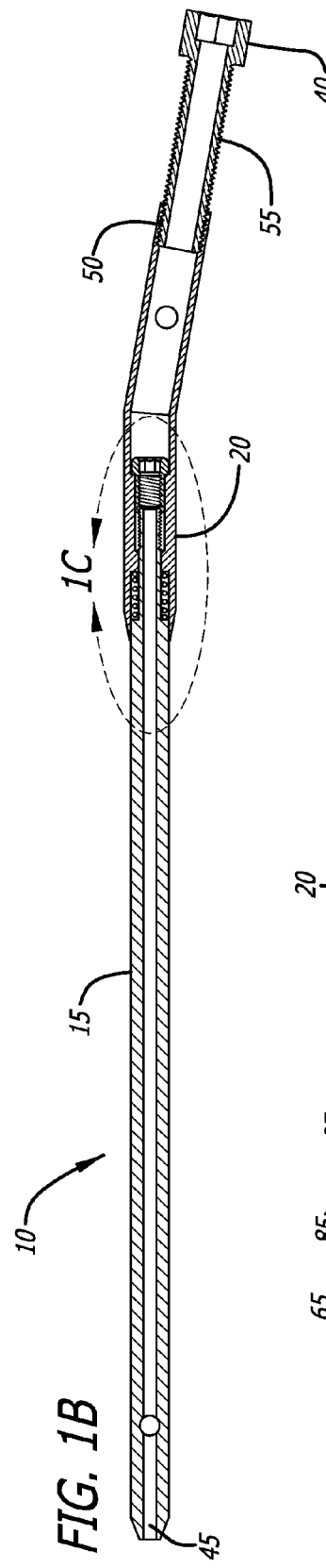
FIG. 1B is a cross-sectional side view of the intramedullary nail of FIG. 1A.

Referring now to FIGS. 1A and 1B, a lumen 45 extends from the end port 25 through the nail 10 to a proximal end 47 of proximal portion 20. When implanting nail 10 within a medullary space of a bone, such as, for example, but not limited to, a tibia or a femur, it is common to use a guidewire to ensure that the nail can be properly positioned, even when the medullary space may be dis-continuous due to the severity of a fracture in the bone. Lumen 45 provides for placing the nail 10 along the guidewire, and then sliding the nail 10 along the guidewire until the nail 10 is properly positioned. The guidewire may then be withdrawn from the nail 10. The distal most end of distal portion 15 may be chamfered to provide reduced friction between the nail and the medullary space of the bone when the nail is inserted into and through the intramedullary space of the bone. The chamfer may be, for example, 15 degrees.

A threaded fastener 40 is also shown in FIGS. 1A and 1B. Fastener 40 engages threads 50 disposed in a proximal end of the proximal portion 20 of intramedullary nail 10. Fastener 40 may be threaded into the threads in the proximal portion to provide a surgeon with a means for removing the nail 10 from the medullary space.

Figure 1C:
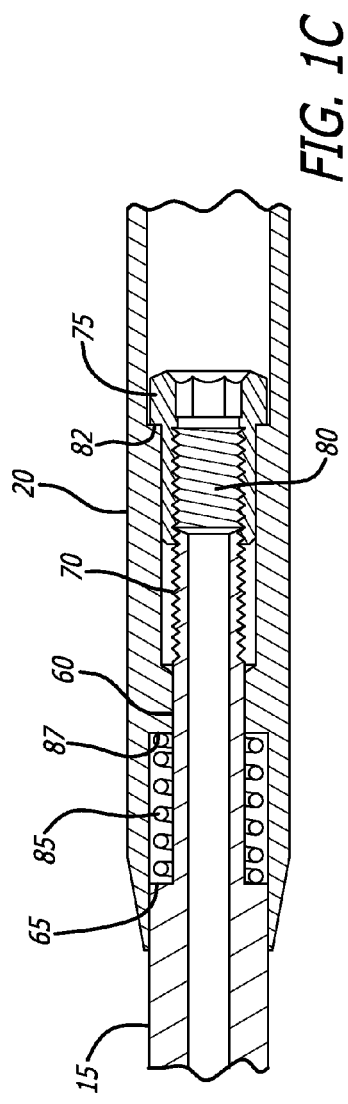
FIG. 1C is a magnified view of a portion of the cross-sectional side view of FIG. 1B showing details of interconnection of the distal and proximal portions of the intramedullary nail of FIG. 1A.

Referring now to FIG. 1C, as well as FIGS. 2A-C and 3A-B, additional details of the distal and proximal portions of the nail 10 are described. A proximal end of the distal portion 15 includes a portion 60 having a reduced diameter compared to the outer diameter of the remainder of the distal portion 15. Given this reduction in diameter, a land 65 is formed at a junction of the reduced portion 60 and the remainder of distal portion 15. A proximal end of reduced diameter portion 60 also has a threaded portion 70 having male threads for engaging corresponding female threads 80 of adjustment nut 75 (FIG. 1C).

Proximal portion 20 (FIGS. 3A-B) includes a distal portion 115 and a proximal portion 120. While lumen 45 extends through both portions, distal portion 115 is offset along a longitudinal axis from proximal portion 120 by an angle phi (Φ) so as to produce a bend in the nail 10 that facilitates placement of the nail through the top of the bone, for example, a tibia bone, and then down through the medullary space of the bone. This angular offset will be dependent on the bone to be stabilized. For example, a femur may require different angulation than a tibia, and thus nails to be used to stabilize a femur will have a different offset than a nail intended for use in a tibia. In one embodiment, for example, intended for implantation within a tibia bone, the angle phi may be 10 to 12 degrees, and preferable 11 degrees.

Proximal portion 120 of proximal portion 20 may also include a bore 35 sized to receive a screw or other fastener for fixing the proximal portion 120 to the portion of bone adjacent proximal portion 120. This allows the proximal portion 20 to be fixed in such a manner to still allow for limited movement between distal portion 15 and proximal portion 20.

As seen in FIG. 3A, the distal portion 115 of proximal portion 20 may also include a chamfered segment 125 located at a distal end 105 of distal portion 115 of proximal portion 20. The angulation Θ of this chamfer may be, for example, 11 degrees.

Referring now FIG. 3B, proximal end 100 of proximal portion 120 of proximal portion 20 is threaded with threads 50 to receive fastener 40 (FIG. 1A). The diameter of lumen 45 in proximal portion 120 of proximal portion has a first diameter that may, but does not have to be, consistent throughout the length of proximal portion 120. This diameter of lumen 45 may remain the same through the angulation between distal portion 115 and proximal portion 120 of proximal portion 20. At some point distal to the beginning of the angulation in the segment designated 135, the diameter of lumen 45 decreases. This reduction in diameter forms a land 82 at the junction of lumen 45 of the proximal portion and the diameter of the lumen of segment 135. At a point distal to land 82, the diameter of lumen 45 through segment 135 is further reduced in segment 145, forming land 84 at the junction between the distal end of segment 135 and the proximal end of segment 145. Finally, at a point distal to land 84, the diameter of the lumen increases at a transition to segment 130. This enlargement of the lumen creates land 87 at the junction between the lumen of segment 145 and the enlarged lumen of segment 130. It will be understood that while exact dimensions of the various lumens and segments have not been specified, they may vary depending on the overall dimensions of the nail 10 and the fasteners used to join proximal portion 20 and distal portion 15, while still providing a lumen through the entire length of the intramedullary nail 10 to allow the nail to be positioned with an intramedullary space of a fractured bone using a guidewire passing through the lumen of the intramedullary nail.

Further detail of the relationship between the various lumen diameters and segments can be understood by referring to the magnified view of FIG. 1C. This view shows how the various lumen diameters and segments of the distal portion 115 of the proximal portion 20 of intramedullary nail 10 cooperate with segment 60 of the proximal end of distal portion 15 of intramedullary 10 to provide for limited motion between the distal portion 15 and proximal portion 20 of the intramedullary nail 10 to promote bone remodeling and healing. As shown, segment 60, including threaded area 70 extend into the lumen located at the distal end 105 of proximal portion 15. In this configuration, a space is formed between land 65 of the distal portion 15 and land 87 of proximal portion 20 of intramedullary nail 10. This space allows a bias means, such as a spring, to be disposed between proximal portion 20 and distal portion 15 of intramedullary nail 10 to bias the two portions apart when the spring is compressed.

Figure 4A:
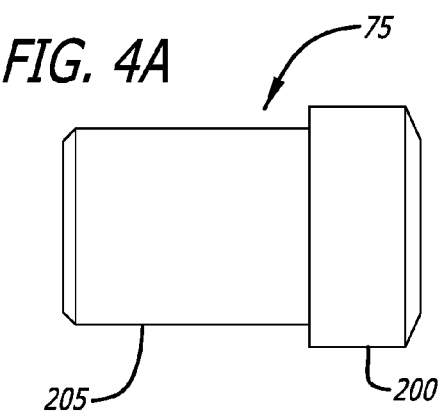
FIG. 4A is a side view of a threaded fastener used to hold the proximal and distal portions of the intramedullary nail of FIG. 1A together
Figure 4B:
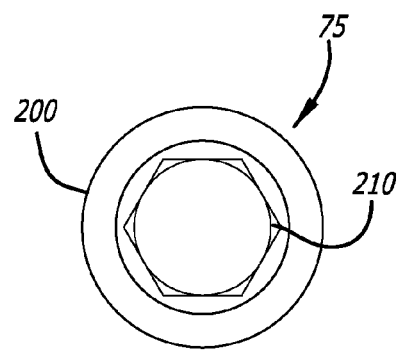
FIG. 4B is a top view of the threaded fastener of FIG. 4A.
Figure 4C:
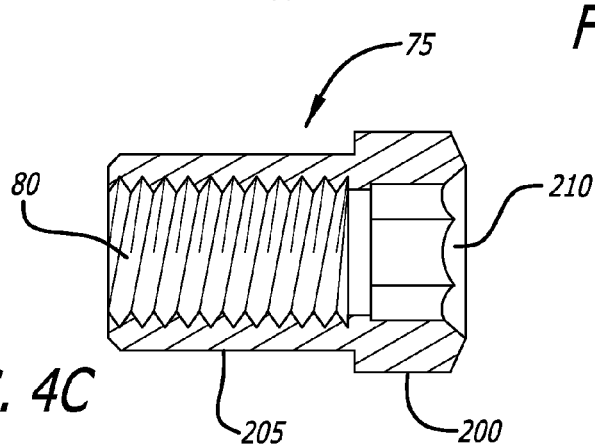
FIG. 4C is a cross-sectional side view of the threaded fastener of FIG. 4A.

Adjustment nut 75 is a threaded nut having a head 200 and a body 205, and is shown in detain in FIGS. 4A-C. See The diameter of the body 205 is sized to be slidingly, rotationally and removably received within the lumen diameter of segment 135 of the proximal portion 115 of proximal portion 20. Head 200 has a diameter that is larger than the diameter of body 205, the diameter being sized to be slidably, rotatably and removably received within the lumen of area 140, and able to pass through the angulation between proximal portion 120 and distal portion 115 of proximal portion 20 of intramedullary nail 10. The distal edge of adjustment nut 75, when inserted into the distal portion 20 of intramedullary nail 10 is advanced and engages threads 70 of distal portion 15 with threads 80. A proximal end of head 200 of adjustment nut 75 includes a means 210 for engaging adjustment nut 75 so that nut 75 may be rotated in a clockwise or counterclockwise direction. Means 210 may be, for example, a hexagonally shaped indentation for receiving a suitably sized hexagonal Allen driver, or it may be slotted, or crossed, or having another suitably shaped indentation for receiving a customized driving tool.

Rotating adjustment nut 75 in a clockwise direction causes the nut to be drawing onto the threads 70, which in turn compresses spring 85 due to the abutment of the distal edge of the head 200 of adjustment nut 75 with land 82. Adjustment nut 75 may continue to be tightened until the spring is completely compressed, or when the distal edge of body 205 of adjustment nut 75 abuts against land 84. Similarly, rotating adjustment nut 75 in a counter-clockwise direction will loosen adjustment nut 75, resulting in distal portion 15 of nail 10 moving away from proximal portion 20 of nail 10 due to the bias imparted by spring 85.

It will be understood that the threads 70 and 80 may be reversed so that rotating adjustment nut 75 in a counter-clockwise direction draws threads 70 into threads 80 to compress spring 85, and rotating adjustment nut 75 in a clockwise direction reduces the compression of spring 85, without departing from the intended scope of the invention.

Additionally, spring 85 is intended as a biasing member, whose function may be carried out by a variety of means besides a spring. For example, spring 85 may be replaced with a reversibly compressible material, such as a polymer. Moreover, the entire arrangement between the proximal portion 20 and distal portion 15 may be constructed in a fashion different from that described above, so long as there is a bias member or device between the two portions that may be adjusted to provide a desired amount of motion between the two portions. In an alternative embodiment, the bias member may be a compound bias member comprising a resilient polymer and a mesh of plastic, metal or other suitable material. In still another embodiment, the bias member may be a compliant membrane.

When the bias means is fully compressed, there is intended to be no relative movement between the distal portion 15 and the proximal portion 20. Loosening adjustment nut 75 reduces the amount of compression of spring 85, allowing for a controlled amount of longitudinal movement of the two portions relative to each other. Alternatively, the bias member may be used to put the fracture under compressing. In this embodiment, the distal portion of the nail is fixed to the bone with a screw, the proximal portion is held while the adjustment nut is tightened, so that the distal portion and proximal portions of the nail pull on the ends of the fracture.

Figure 5A:
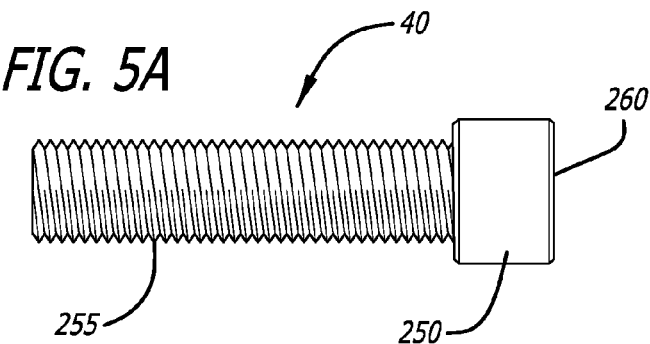
FIG. 5A is a side view of a threaded fastener that may be inserted into a proximal end of the proximal portion of the intramedullary nail of FIG. 1A.
Figure 5B:
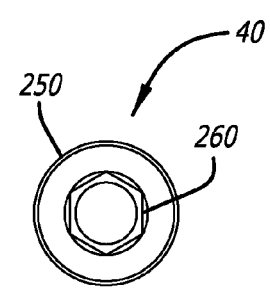
FIG. 5B is a top view looking down at the proximal end of the threaded fastener of FIG. 5A.
Figure 5C:
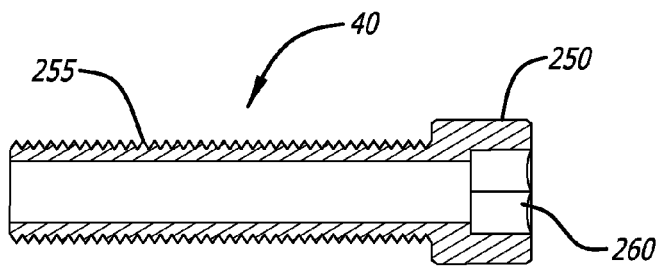
FIG. 5C is a cross-sectional side view of the threaded fastener of FIG. 5A.

FIGS. 5A-C illustrate details of fastener 40. Fastener 40 has a head 250 and a threaded body 255. The threads of threaded body 255 are sized to engage threads 50 disposed within the bore of proximal end 100 of proximal portion 20. This allows fastener 40 to be threaded into proximal end 100 to provide a means for extracting nail 10 from a medullary space. Head 250 of fastener 40 also includes an indentation 260 shaped and sized to receive a driver, such as, for example, but not limited to, a hexagonally shaped driver, to provide for rotating the fastener 40 in clockwise and counter-clockwise directions.

In another embodiment, fastener 40 may be formed in the shape of a "handle" that has a threaded distal end and a proximal end having a handle-like shape to facilitate installation of the nail. For example, the proximal end of the handle shaped fastener may be, for example, in the shape of a "T" shape or the like. During installation, the distal end of the fastener would be threaded into the nail, and the nail placed at the entrance of the intramedullary canal. The handle shape of the proximal end of the fastener provides an area or surface which could be struck by a striking implement, and would facilitate driving the nail in the intramedullary canal of the bone. The striking implement could be, for example, a hammer, mallet or the like. The handle-like shape of the proximal end of the fastener 40 could then be used to facilitate rotation of the fastener to remove the fastener from the intramedullary nail 10 once the nail was properly positioned and stabilized within the intramedullary space of the bone.

The embodiment of the intramedullary nail described above is constructed of materials know to be biocompatible. Examples of suitable materials are various types of stainless steel or titanium alloys, such as Ti—6Al—4V, Cobalt chromium or the like.

The intramedullary nail will typically be cylindrical in shape, but may be an elongated body having another shape, such as a hexagonal, ovoid or other suitable external shape depending on the needs of the surgeon. The distal and proximal portions 15, 20 will typically be arranged in a telescoping relationship. Moreover, a means for maintaining the proximal and distal portions 15, 20 of intramedullary nail 10 in alignment may also be provided, such as by using a spline mounted on one of the portions to engage a keyway disposed in or on the other portion. In the case where the nail is not cylindrical, the shape of the portions may be self-aligning, such as where the overall outer profile of the nail is hexagonal.

Figure 6A:
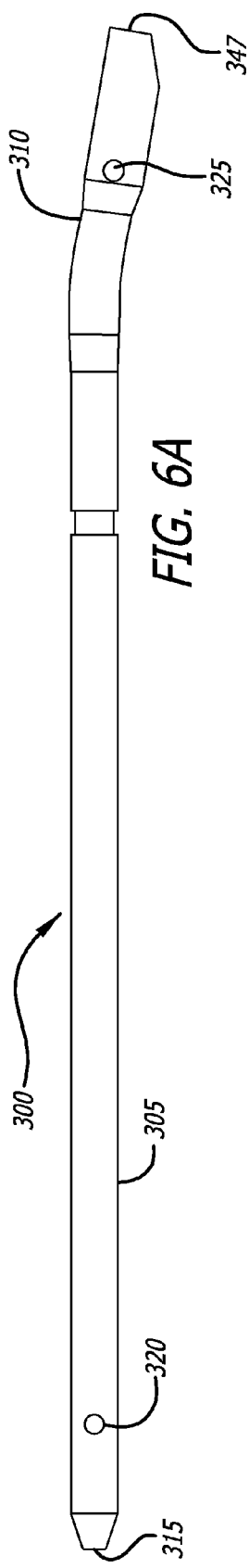
FIG. 6A is a side view of an alternative embodiment of an intramedullary nail in accordance the present invention.

Referring now to FIG. 6A another exemplary embodiment of an intramedullary nail 300 in accordance with the present invention is shown. Intramedullary nail 300 includes a distal portion 305 and a proximal portion 310. As will be discussed in more detail below, the distal and proximal portions are engaged in a manner that allows each portion to move a limited amount independently of the other portion.

Distal portion 305 includes an end port 315 disposed at a distal end of the distal portion 305. A fixation hole 320 is also disposed near the distal end of distal portion 305. Fixation hole 320 is sized to receive a screw or other fastener that may be used to attached distal portion 305 to bone surrounding distal portion 305 when the intramedullary nail 300 is positioned within the medullary space of a bone so as to fixate and stabilize a fracture in the bone.

Figure 6B:
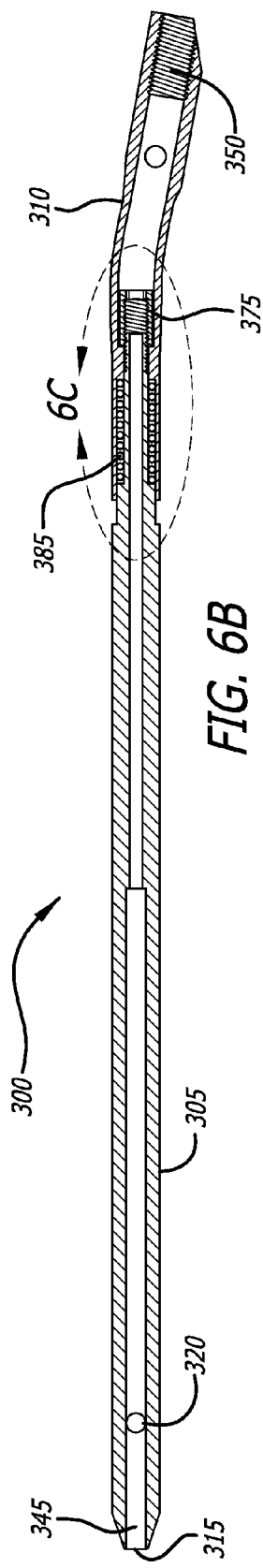
FIG. 6B is a cross-sectional side view of the intramedullary nail of FIG. 6A.

Referring now to FIGS. 6A-B, a lumen 345 extends from the end port 315 through the intramedullary nail 300 to a proximal end 347 of proximal portion 310 to facilitate implanting the intramedullary nail using a guidewire, as described above. The distal most end of distal portion 305 may be chamfered to provide reduced friction between the nail and the medullary space of the bone when the nail is inserted into and through the intramedullary space of the bone. The chamfer may be, for example, 15 degrees, but other angulations may be used to suit the particular bone size or fracture type into which the intramedullary nail is being implanted.

The interior of proximal end 347 of the proximal portion 310 of intramedullary nail 300 may also include threads 350. A fastener may be threaded into the threads 350 to provide a surgeon with a means for removing the nail 300 from the intramedullary space of the bone.

Figure 6C:
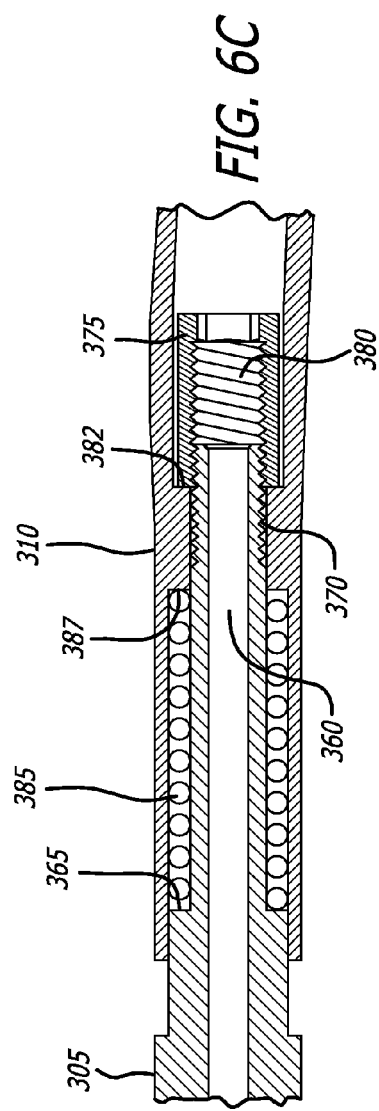
FIG. 6C is a magnified view of a portion of the cut-away view showing details of interconnection of the distal and proximal portions of the intramedullary nail of FIG. 6A.
Figure 7A:
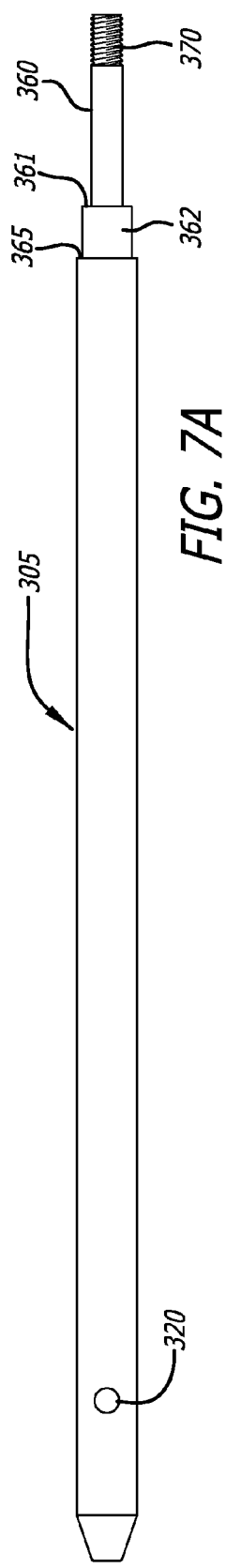
FIG. 7A is a side view of a distal portion of the intramedullary nail of FIG. 6A.
Figure 7B:
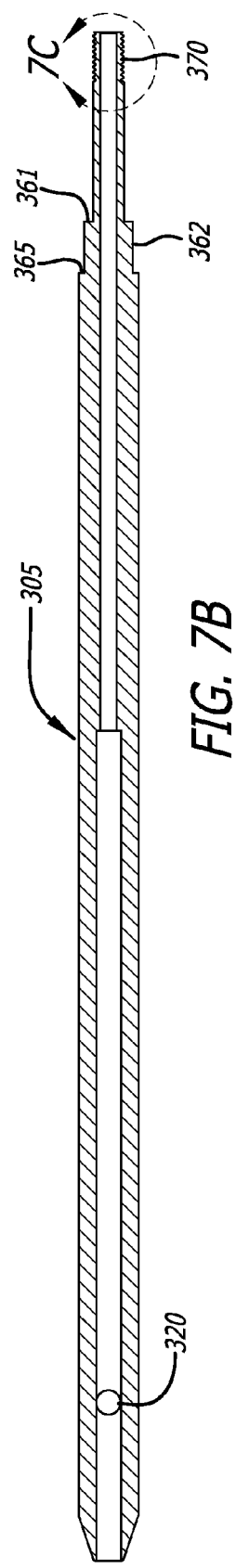
FIG. 7B is a cross-sectional side view of the distal portion of the intramedullary nail of FIG. 7A.
Figure 7C:
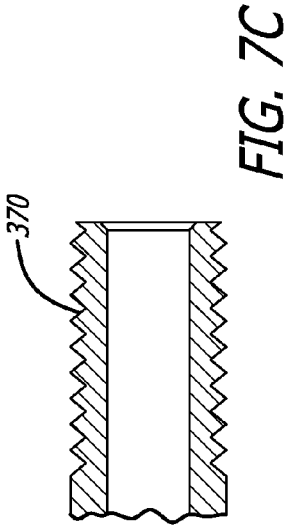
FIG. 7C is a magnified cross-sectional side view of a threaded proximal end of the distal portion of the intramedullary nail shown in of FIG. 7B.

Referring now FIG. 6C, as well as FIGS. 7A-C and 8A-B, additional details of the distal and proximal portions of the nail 300 are described. A proximal end of the distal portion 305 of nail 300 includes a portion 360 having a reduced diameter compared to the diameter of the remainder of the distal portion 305. Given this reduction in diameter, a land 361 is formed at a junction of the reduced portion 360 and portion 362. Portion 362 has an increased diameter relative to portion 360, but that diameter is less than the outer diameter of distal portion 305. The junction between portion 362 and the remainder of distal portion 305 thus forms a land 365. A proximal end of portion 360 also has a threaded portion 370 having male threads for engaging corresponding female threads 380 of adjustment nut 375 (FIG. 6C).

Proximal portion 310 (FIGS. 8A-B) includes a distal portion 415 and a proximal portion 420. While lumen 45 extends through both portions, distal portion 415 is offset along a longitudinal axis from proximal portion 420 by an angle $phi_2$ ($\Phi_2$) so as to produce a bend in the nail 300 that facilitates placement of the nail through the top of the bone, for example, a tibia bone, and then down through the medullary space of the bone. This angular offset will be dependent on the bone to be stabilized. For example, a femur may require different angulation than a tibia, and thus nails to be used to stabilize a femur will have a different offset than a nail intended for use in a tibia. In one embodiment, for example, intended for implantation within a tibia bone, the angle $phi_2$ may be 10 degrees.

Figure 8A:
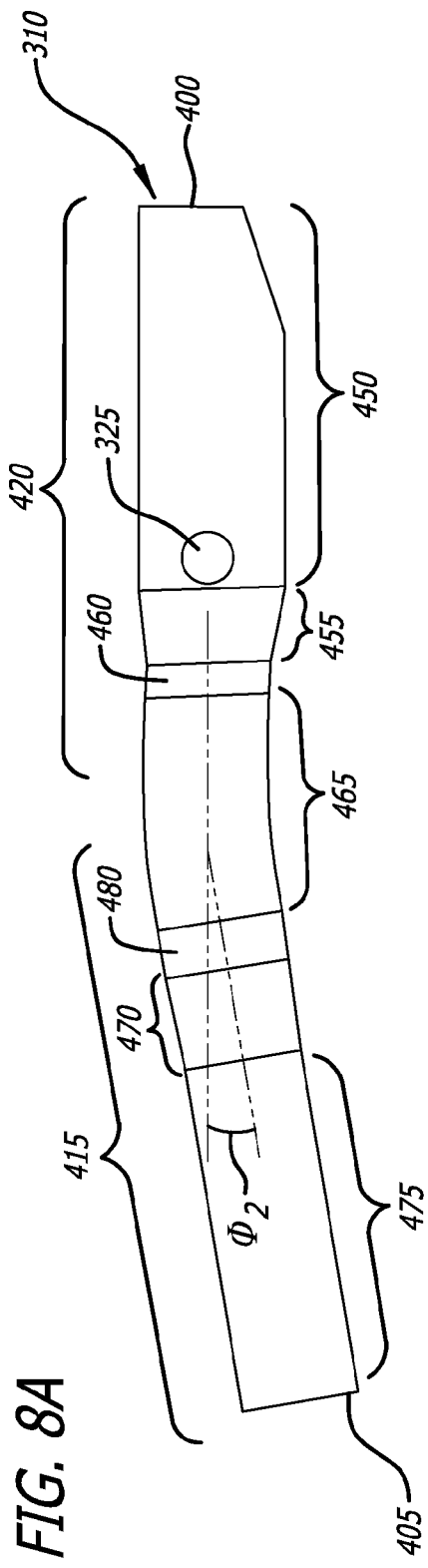
FIG. 8A is a side view of the proximal portion of the intramedullary nail of FIG. 6A.
Figure 8B:
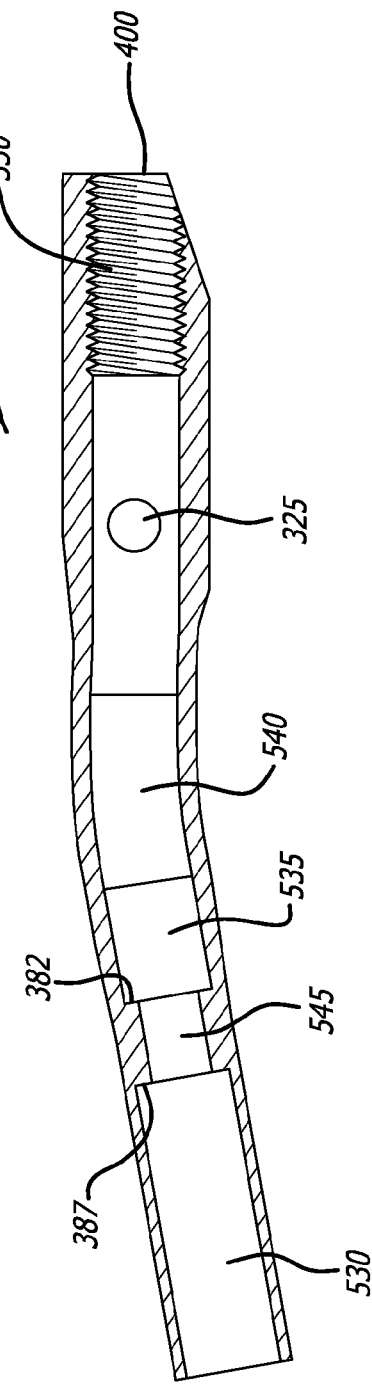
FIG. 8B is a cross-section of the proximal portion of the intramedullary nail of FIG. 8B showing internal details of the embodiment.

As is evident from FIGS. 8A-B, besides major sections portion 415 and portion 420, proximal portion 310 may include additional segments, such as segment 450, 455, 460, 465, 470, 475 and 480. The geometric shape of these segments may be consistent with the shapes of portions 415 and 420, or they may be varied to facilitate use of the intramedullary nail 300. In the embodiment shown, for example, segment 450, which forms the most proximal segment of portion 420 of intramedullary nail 300 may be a cylinder having a constant outer diameter, but also may have a chamfer disposed on the proximal end 400 of segment 450. This chamfer ensures that once the nail is implanted in a bone, the proximal end of the nail will not unduly extend from the top of the bone, but will instead more readily blend with the contour of the bone.

As shown in FIG. 8A, segment 455 may have a proximal end that has an outer diameter substantially equal to the outer diameter of the distal end of segment 450. The outer diameter of segment 455 tapers along its length to a reduced outer diameter at its distal end. The taper may be, for example, but not limited to, five degrees.

In some embodiments, such as the embodiment of FIG. 8A, proximal portion 310 may also include a segment 460. This segment may have a consistent outer diameter, beginning at the distal end of segment 455 and ending at the proximal end of segment 465, or the outer diameter may change depending on the design of the nail.

Segment 465 includes angulation $phi_2$, as described above. There may also be a segment 480 interposed between segment 470 and segment 465. The length and outer diameter of this segment are dependent upon the over length of the nail and the design requirements as described above.

Segment 470 may also be included. As shown, segment 470 may taper from its proximal end to its distal end, as required for the design of the nail. In the example shown, the taper is two degrees. Segment 475 comprises the distal end of proximal portion 310.

It will be understood by those skilled in the art that the various segments described above may or not be present in an embodiment of the intramedullary nail of the present invention. For example, depending on the length of the nail, one or both of segments 460 and 480 may be omitted without departing from the scope of the invention. Additionally, segments 470 and 455 may be need to be tapered, and indeed, may be omitted from the nail, depending on the design of the nail for a particular bone size or length or fracture situation.

Proximal portion 420 of proximal portion 310 may also include a bore 325 sized to receive a screw or other fastener for fixing the proximal portion 420 to the portion of bone adjacent proximal portion 420. This allows the proximal portion 420 to be fixed in such a manner to still allow for limited movement between distal portion 305 and proximal portion 310.

Referring now FIG. 8B, proximal end 400 of proximal portion 310 is threaded with threads 350 to receive a fastener or handle-like tool as described above to facilitate installation and removal of intramedullary nail 300 from the intramedullary space of a bone. The diameter of lumen 345 in proximal portion 420 of proximal portion 310 has a first diameter that may, but does not have to be, consistent throughout the length of proximal portion 420. This diameter of lumen 345 may remain the same through the angulation between distal portion 415 and proximal portion 420 of proximal portion 310.

At some point distal to the beginning of the angulation in the segment designated 535, the diameter of lumen 345 decreases. This reduction in diameter forms a land 382 at the junction of lumen 345 at the proximal end of segment 545 and the diameter of the lumen at the distal end of segment 135. The diameter of lumen 345 increases at junction between the distal end of segment 545 and the proximal end of segment 530. This change in lumen diameter results in the formation of a land 387.

It will be understood that while exact dimensions of the various lumens and segments have not been specified, they may vary depending on the overall dimensions of the nail 300 and the fastener used to join proximal portion 310 and distal portion 305, while still providing a lumen through the entire length of the intramedullary nail 300 to allow the nail to be positioned with an intramedullary space of a fractured bone using a guidewire passing through the lumen of the intramedullary nail.

Further detail of the relationship between the various lumen diameters and segments can be understood by referring to the magnified view of FIG. 6C. This view shows how the various lumen diameters and segments of the distal portion 415 of the proximal portion 310 of intramedullary nail 300 cooperate with area 360 of the proximal end of distal portion 305 of intramedullary 300 to provide for limited motion between the distal portion 305 and proximal portion 310 of the intramedullary nail 300 to promote bone remodeling and healing. As shown, area 360 includes threaded area 370 extends into the lumen located at the distal end 405 (FIG. 8A) of proximal portion 310. In this configuration, a space is formed between land 365 of the distal portion 305 and land 387 of proximal portion 310 of intramedullary nail 300. This space allows a bias means, such as a spring, to be disposed between proximal portion 3100 and distal portion 305 of intramedullary nail 300 to bias the two portions apart when the spring is compressed.

Figure 9A:
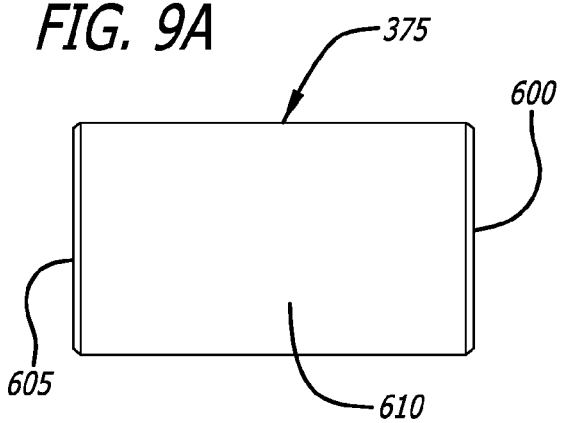
FIG. 9A is a side view of an embodiment of a threaded fastener used to hold the proximal and distal portions of the intramedullary nail of FIG. 6A together
Figure 9B:
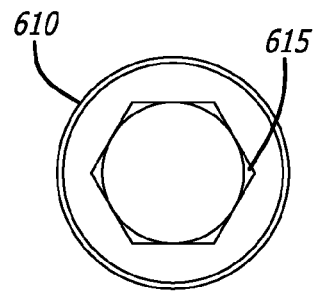
FIG. 9B is a top view of the threaded fastener of FIG. 9A.
Figure 9C:
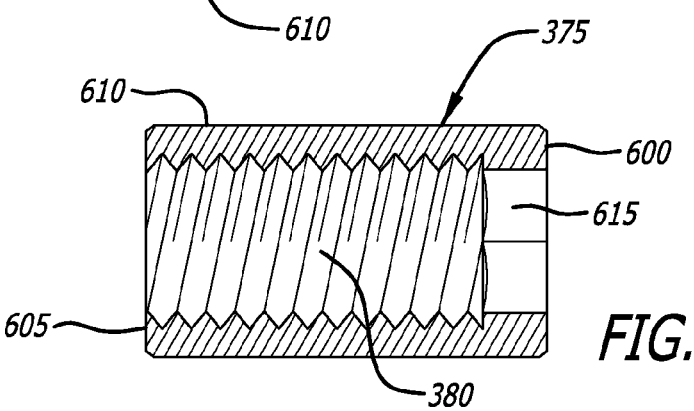
FIG. 9C is a cross-sectional side view of the threaded fastener of FIG. 9A.

Adjustment nut 375 is a threaded nut having a proximal end 600, a distal end 605, and a body 610, and is shown in detail in FIGS. 9A-C. The diameter of the body 615 is sized to be slidingly, rotationally and removably received within the lumen diameter of segment 535 of the proximal portion 415 of proximal portion 310, and is able to pass through the angulation between proximal portion 420 and distal portion 415 of proximal portion 310 of intramedullary nail 300. In this embodiment, the outer diameter of body 610 is constant from proximal end 600 to distal end 605, although some deviation may be allowed so long as the adjustment nut 375 is able to slide through lumen 345.

Adjustment nut 375, when inserted into the distal portion 305 of intramedullary nail 300 engages threads 370 of distal portion 305 with threads 380. The proximal end of adjustment nut 375, as shown in FIG. 9B, includes a means 615 for engaging adjustment nut 375 so that nut 375 may be rotated in a clockwise or counterclockwise direction with a suitable tool. Means 615 may be, for example, a hexagonally shaped indentation for receiving a suitably sized hexagonal Allen driver, or it may be slotted, or crossed, or having another suitably shaped indentation for receiving a customized driving tool.

Rotating adjustment nut 375 in a clockwise direction causes the nut to be drawing onto the threads 370, which in turn compresses spring 385 due to the abutment of the distal end 605 of adjustment nut 375 with land 382. Adjustment nut 375 may continue to be tightened until the spring is completely compressed. Similarly, rotating adjustment nut 375 in a counter-clockwise direction will loosen adjustment nut 375, resulting in distal portion 305 of nail 300 moving away from proximal portion 310 of nail 300 due to the bias imparted by spring 385.

It will be understood that the threads 370 and 380 may be reversed so that rotating adjustment nut 375 in a counterclockwise direction draws threads 370 into threads 380 to compress spring 385, and rotating adjustment nut 375 in a clockwise direction reduces the compression of spring 385, without departing from the intended scope of the invention. As described above, while bias means is shown as spring 375 in this embodiment, other biasing devices or materials may be utilized, such as a reversibly compressible polymer, and the like.

Figure 10A:
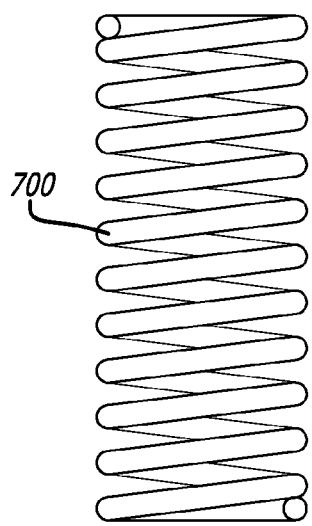
FIG. 10A is a side view of a compressible/extensible member for providing a bias between the distal and proximal portions of an embodiment of an intramedullary nail in accordance with the present invention.
Figure 10B:
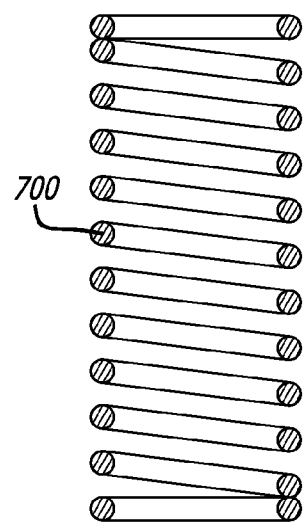
FIG. 10B is a cross-sectional side view of the compressible/extensible member of FIG. 10A.

FIGS. 10A-C illustrate one embodiment of a biasing device or means 700 that may be used with the various embodiments of the present invention. In this embodiment, the biasing means 700 is depicted as a spring. As noted above, however, other types of biasing members or devices or means may be employed. Where a spring is used, the coils of the spring may be consistent, or the spring may be formed in such a way that the spring constant K of the spring varies along the length of the spring, thus imparting variable biasing force depending on how much the spring is compressed or extended. This variance may be accomplished in various way, as is known to those skilled in the art. For example, the spacing between coils of the spring may differ along the longitudinal length of the spring, or the diameter of the coil wire may vary.

In still another embodiment, the size and/or resiliency of the bias member may be selected depending on bone size and patient weight to achieve a desired load-deflection. Different bias members could have different load-deflection curves, allowing a surgeon to choose the bias member that fits a particular situation, including fracture type, complexity, patient weight and bone dimensions.

In yet another embodiment, any of the various embodiments of the nail of the present invention may be covered or coated with a suitable biocompatible material which may have healing enhancement properties. The nail may be coated with, for example, but not limited to, zinc. Alternatively, the nail may be coated with a material or drug, or a combination of material or drug, to enhance bone formation or to promote healing of the fracture. In still another embodiment, the outer surface of the nail of any of the various embodiments may be textured to enhance implantation, or hold a coating or drug or combination of the two to enhance healing of the fracture.

Various procedures for using an intramedullary nail of the present invention are described in the literature and are well known in the art. For example, an method for reducing a tibial shaft fracture is contained in Trafton, Peter G. "Tibial Shaft Fractures." (Elsevier Science (USA) 2003), the entirety of which is intended to be incorporated by reference herein.

Other information discussing the scientific rationale supporting the advancement over the prior art represented by the inventors various embodiments of the present invention are also attached hereto, and are intended to be incorporated in their entirety by reference herein.

While several particular forms of the invention have been illustrated and described, it will be apparent that various modifications can be made without departing from the spirit and scope of the invention.

I claim:

1. An intramedullary nail for placement in a bone, comprising:
    a distal portion having a distal end having a first diameter and a proximal end having a second diameter, the second diameter of the proximal end of the distal portion being less than the first diameter of the distal end of the distal portion, the distal end of the distal portion and the proximal end of the distal portion being coaxially disposed about a longitudinal axis of the distal portion, the distal portion also having a first land created at a point where the first diameter of the distal end of the distal portion meets the second diameter of the proximal end of the distal portion;
    a proximal portion having a proximal end and a distal end, the distal end of the proximal portion telescopically arranged around the proximal end of the distal portion, the first land, and a portion of the distal end of the distal portion, the proximal portion being moveably engaged with the proximal end of the distal portion, the distal end of the proximal portion having a first section having a first diameter sized to slide over the first diameter of the distal end of the distal portion, the first section having a second land formed by a second diameter of the first section, the second diameter of the first section being less than the first diameter of the first section; a space defined by the first land of the distal portion and the second land of the proximal portion disposed between the first diameter of the first section of the distal end of the proximal portion and the second diameter of the proximal end of the distal portion;
    a reversibly compressible bias member disposed in the space between first land and the second land for biasing the distal and proximal portions apart along the longitudinal axis; and
    an adjusting assembly configured to engage the distal and proximal portions such that actuation of the adjusting assembly results in providing for a selected overall maximum length of the arrangement of the distal and proximal portions along the longitudinal axis, the overall maximum length being selected before the distal and proximal portions are fixated to the bone, and a selected amount of reversible movement along the longitudinal axis between the proximal and distal portions, such that the arrangement of the proximal and distal portions has an uncompressed length equal to the selected overall maximum length and a compressed length that is less than the selected overall maximum length when a compressive force is applied along the longitudinal axis when the nail is fixed within with the bone.

2. The nail of claim 1, further comprising an alignment assembly that engages the proximal and distal portions in a manner to maintain an alignment between the proximal and distal portions.

3. The nail of claim 1, wherein an outer surface of the distal and proximal portions is covered with a material that enhances healing of a fracture.

4. The nail of claim 3, wherein the material is zinc.

5. The nail of claim 1, wherein the bias member is a spring.

6. The nail of claim 1, wherein the bias member is a compliant membrane.

7. An intramedullary nail configured for insertion into a fractured long bone of a body and also configured to provide a selected amount of reversible movement along a longitudinal axis between a proximal and distal portion of the fractured bone, comprising:
    a distal portion having a distal end having a first diameter and a proximal end having a second diameter, the second diameter of the proximal end of the distal portion being less than the first diameter of the distal end of the distal portion, the distal end of the distal portion and the proximal end of the distal portion being coaxially disposed about a longitudinal axis of the distal portion, the distal portion also having a first land created at a point where the first diameter of the distal end of the distal portion meets the second diameter of the proximal end of the distal portion;
    a proximal portion
        having a proximal end and a distal end, the distal end of the proximal portion telescopically arranged around the proximal end of the distal portion, the first land, and a portion of the distal end of the distal portion, the proximal portion being moveably engaged with the proximal end of the distal portion, the distal end
        of the proximal portion having a first section diameter sized to slide over the first diameter of the distal end of the distal portion, the first section having a second land formed by a second diameter of the first section, the second diameter of the first section being less than the first diameter of the first section; a space defined by the first land of the distal portion and the second land of the proximal portion disposed between the first diameter of the first section of the distal end of the proximal portion and the second diameter of the proximal end of the distal portion;
    an adjusting assembly disposed between the distal and proximal portions, the adjusting assembly configured to allow a user to select an uncompressed longitudinal length of the arrangement of the distal and proximal portions before the distal and proximal portions of the intramedullary nail are fixated to the proximal and distal portions of the bone; and
    a reversibly compressible bias member disposed in the space between the first land and the second land for biasing the distal and proximal portions apart along the longitudinal axis such that the arrangement of the distal and proximal portions has a compressed longitudinal length less than the selected uncompressed longitudinal length when the arrangement is compressed, the reversibly compressible bias member causing the arrangement of the distal and proximal portions to return to the selected uncompressed longitudinal length when the arrangement is uncompressed when the nail is fixed within the bone.

8. The intramedullary nail of claim 7, further comprising:
    a proximal bone fixation point disposed on the proximal portion and a distal bone fixation point disposed on the distal portion, and wherein the selected uncompressed longitudinal length defines a maximum separation between the proximal and distal fixation points, and wherein compression of the arrangement of proximal and distal portions results in a reduced separation between the proximal and distal fixation points, the separation between the proximal and distal fixation points returning to the maximum separation when the proximal and distal portions are not compressed.

9. The intramedullary nail of claim 7, wherein the bias member is a spring.

10. The intramedullary nail of claim 7, wherein the bias member is a compliant membrane.

11. The intramedullary nail of claim 7, further comprising an alignment assembly that engages the proximal and distal portions in a manner to maintain an alignment between the proximal and distal portions.

12. An intramedullary nail for placement inside a bone having a fracture defining a distal portion and a proximal portion of the bone, the fracture having a proximal margin disposed at a distal end of the proximal portion of the bone and a distal margin disposed at a proximal end of the distal portion of the bone, comprising:

a distal portion having a distal fixation point for fixing the distal portion to the distal portion of the bone and also having a distal end having a first diameter and a proximal end having a second diameter, the second diameter of the proximal end of the distal portion being less than the first diameter of the distal end of the distal portion, the distal end of the distal portion and the proximal end of the distal portion being coaxially disposed about a longitudinal axis of the distal portion, the distal portion also having a first land created at a point where the first diameter of the distal end of the distal portion meets the second diameter of the proximal end of the distal portion;

a proximal portion having a proximal end and a distal end, the distal end of the proximal portion telescopically arranged around the proximal end of the distal portion, the first land, and a portion of the distal end of the distal portion, such that the proximal end of the distal portion extends within the proximal portion for a length that is less than the total length of the proximal portion, the proximal portion having a proximal fixation point for fixing the proximal portion to the proximal portion of the bone; the proximal portion being moveably engaged with the proximal end of the distal portion, the distal end of the proximal portion having a first section having a first diameter sized to slide over the first diameter of the distal end of the distal portion, the first section having a second land formed by a second diameter of the first section, the second diameter of the first section being less than the first diameter of the first section; a space defined by the first land of the distal portion and the second land of the proximal portion disposed between the first diameter of the first section of the distal end of the proximal portion and the second diameter of the proximal end of the distal portion;

an adjusting assembly disposed between the distal and proximal portions, the adjusting assembly configured to allow a user, before the intramedullary nail is fixed to the proximal and distal portions of the bone, to select an uncompressed longitudinal length of the arrangement of the distal and proximal portion, the selected uncompressed longitudinal length defining a maximum separation between the proximal and distal fixation points; and a reversibly compressible bias member disposed in the space between the first land and the second land for biasing the distal and proximal portions apart along the longitudinal axis such that compression of the arrangement of proximal and distal portions results in a reduced separation between the proximal and distal fixation points when the nail is fixed within a bone, the separation between the proximal and distal fixation points returning to the maximum separation when the proximal and distal portions are not compressed when the nail is fixed within the bone.

13. The intramedullary nail of claim 12, further comprising an alignment assembly that engages the proximal and distal portions in a manner to maintain an alignment between the proximal an distal portions.

14. The intramedullary nail of claim 12, wherein the maximum separation of the proximal and distal fixation points is selected by the user to provide a maximum separation between the proximal and distal margins of the fracture.

\* \* \* \* \*